United States Patent
Kwon et al.

(10) Patent No.: US 12,312,623 B2
(45) Date of Patent: May 27, 2025

(54) METHOD FOR PRODUCING PSICOSE FROM FRUCTOSE-CONTAINING SUBSTRATE

(71) Applicant: SAMYANG CORPORATION, Seoul (KR)

(72) Inventors: Soun Gyu Kwon, Cheongju-si (KR); Hye Jung Kim, Daejeon (KR); Bu-Soo Park, Daejeon (KR); Chong Jin Park, Daejeon (KR); Kang Pyo Lee, Seoul (KR); Hee Soon Cheon, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 1258 days.

(21) Appl. No.: 15/774,340

(22) PCT Filed: Nov. 16, 2016

(86) PCT No.: PCT/KR2016/013197
§ 371 (c)(1),
(2) Date: May 8, 2018

(87) PCT Pub. No.: WO2017/086690
PCT Pub. Date: May 26, 2017

(65) Prior Publication Data
US 2023/0183764 A1     Jun. 15, 2023

(30) Foreign Application Priority Data
Nov. 16, 2015  (KR) .......................... 10-2015-0160710

(51) Int. Cl.
| | | |
|---|---|---|
| *C12N 11/00* | (2006.01) | |
| *C12N 9/90* | (2006.01) | |
| *C12N 11/10* | (2006.01) | |
| *C12P 19/02* | (2006.01) | |

(52) U.S. Cl.
CPC ................ *C12P 19/02* (2013.01); *C12N 9/90* (2013.01); *C12N 11/10* (2013.01); *C12Y 501/03* (2013.01)

(58) Field of Classification Search
CPC .. C12N 9/90; C12P 19/02; C12P 19/24; C12P 19/18; C12Y 301/03011; C12Y 503/01008; C07H 1/06; C07H 3/02
USPC ............................................ 435/252.22, 105
See application file for complete search history.

(56) References Cited

U.S. PATENT DOCUMENTS

| | | |
|---|---|---|
| 8,030,035 B2 | 10/2011 | Oh et al. |
| 8,524,888 B2 | 9/2013 | Lee et al. |
| 8,735,106 B2 | 5/2014 | Hong et al. |
| 2015/0210996 A1 | 7/2015 | Woodyer et al. |

FOREIGN PATENT DOCUMENTS

| | | |
|---|---|---|
| CN | 102250157 | 11/2011 |
| CN | 102869783 | 1/2013 |
| CN | 104769109 | 7/2015 |
| EP | 2749645 | 7/2014 |
| JP | 3711296 | 11/2005 |
| JP | 2011-206054 | 10/2011 |
| JP | 2013-501519 | 1/2013 |
| KR | 10-0864399 | 10/2008 |
| KR | 10-2011-0035805 | 4/2011 |
| KR | 10-2011-0108185 | 10/2011 |
| KR | 101318422 | 10/2013 |
| KR | 10-2014-0021974 | 2/2014 |
| KR | 10-2014-0080282 | 6/2014 |
| KR | 10-1455759 | 10/2014 |
| KR | 10-1473918 | 12/2014 |
| KR | 10-1616050 | 4/2016 |
| WO | 2015-032761 | 3/2015 |
| WO | 2015-099256 | 7/2015 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
EPO, Third Party Observation of Application No. EP 16866642.8 TPO , Sep. 2, 2019.
Byung-Chul Lim et al., "A stable immobilized D-psicose 3-epimerase for the production of D-psicose in the presence of borate", Process Biochemistry 44 (2009) 822-828.
EPO, Third Party Observation (TPO) of Application No. 16866642. 8. dated Jul. 10, 2019.
EPO, A Extended European Search Report of EP 16866642.8 dated on Mar. 14, 2019.
Li Xiao-bo, et al., "Immobilization of D-psicose 3-epimerase on chitosan for D-psicose conversion", Science and Technology of Food Industry, Dec. 31, 2013, 158-162.
J. Park et al., "Construction of Heat-Inducible Expression Vector of Corynebacterium glutamicum and C. ammoniagenes: Fusion of λ Operator with Promoters Isolated from C. ammoniagenes", Journal of Microbiology and Biotechnology, vol. 18, No. 4, pp. 639-647, 2008.

(Continued)

*Primary Examiner* — Robert B Mondesi
*Assistant Examiner* — Mohammad Y Meah
(74) *Attorney, Agent, or Firm* — LEX IP MEISTER, PLLC

(57) ABSTRACT

The present invention relates to a method of obtaining a psicose-containing product from a fructose-containing substrate with high productivity in a short time on an industrial scale by an immobilization reaction using a biocatalyst for producing a psicose, and a method of preparing a liquid type or powder type of psicose by isolating the psicose-containing product obtained by the method and preparing a psicose continuously by inputting a byproduct of isolation process into a process of production of psicose-containing product.

15 Claims, 4 Drawing Sheets

Specification includes a Sequence Listing.

(56) References Cited

OTHER PUBLICATIONS

JPO, Office Action of JP 2018-525587 dated Jun. 13, 2019, total 3 pages.
JPO, Office Action of JP 2018-525587 dated Jan. 31, 2020, total 3 pages.

* cited by examiner

[FIG. 1]
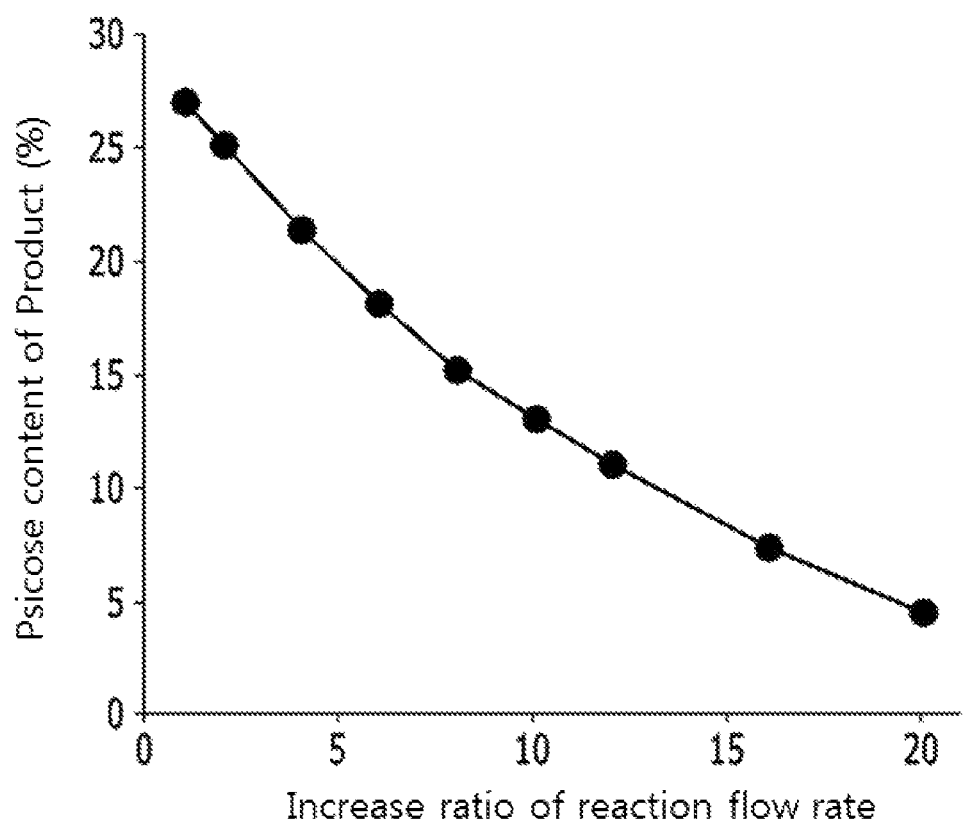

[FIG. 2]

Equation: Polynomial, Quadratic
f=y0+a*x+b*x^2

Results for the Overall Best-Fit Solution:

| R | Rsqr | Adj Rsqr | Standard Error of Estimate | | |
|---|---|---|---|---|---|
| 0.9995 | 0.9991 | 0.9988 | 0.2537 | | |
| | Coefficient | Std. Error | t | P | VIF |
| y0 | 26.7829 | 0.2192 | 122.1627 | <0.0001 | 6.7233< |
| a | -3.6566 | 0.1042 | -35.1008 | <0.0001 | 43.0514< |
| b | 0.1418 | 0.0099 | 14.3734 | <0.0001 | 24.7607< |

【FIG. 3】
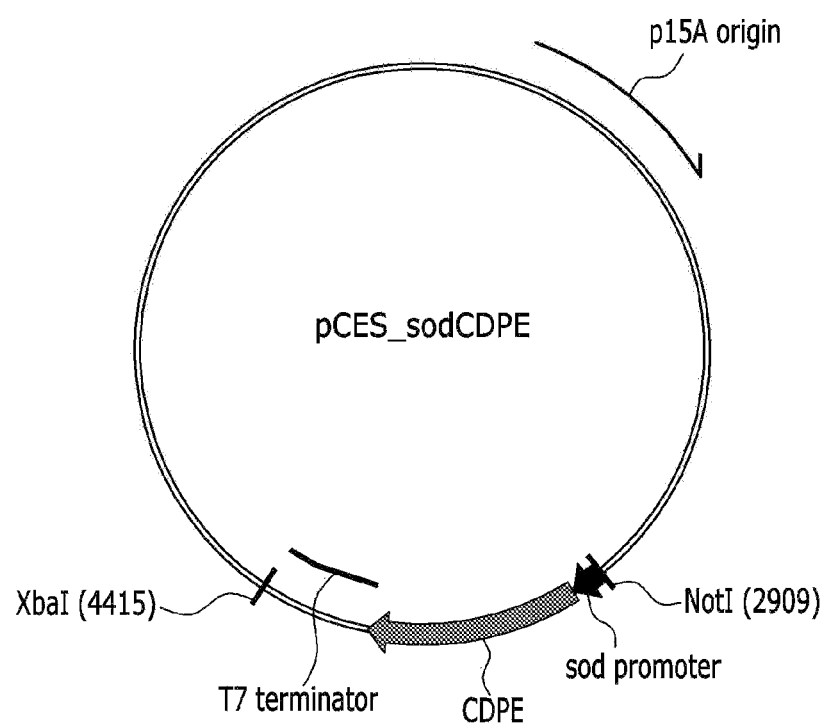

[FIG. 4]
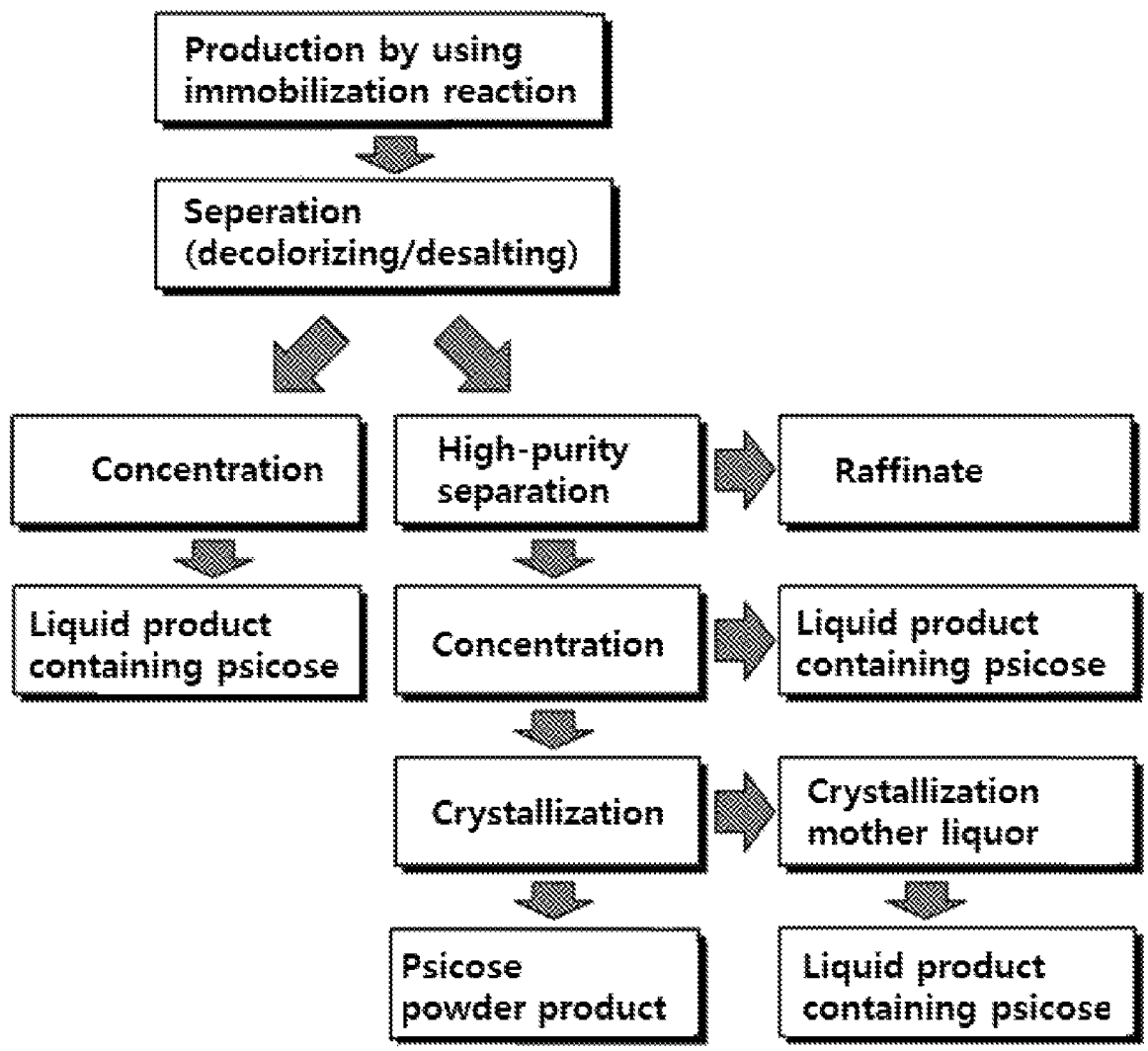

SEQUENCE LISTING

<160> NUMBER OF SEQ ID NOS: 9

<210> SEQ ID NO 1
<211> LENGTH: 356

```
<212> TYPE: DNA
<213> ORGANISM: Artificial Sequence
<220> FEATURE:
<223> OTHER INFORMATION: sod promoter (6)

<400> SEQUENCE: 1
aagcgcctca tcagcggtaa ccatcacggg ttcgggtgcg aaaaaccatg ccataacagg      60
aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaagatgt atatgctcgg tgcggaaacc tacgaaagga tttttttaccc    300 atggctgtat acgaactccc agaactcgac tacgcatacg acgaaaggat tacaaa        356

<210> SEQ ID NO 2
<211> LENGTH: 93
<212> TYPE: DNA
<213> ORGANISM: Artificial Sequence
<220> FEATURE:
<223> OTHER INFORMATION: Tac1 promoter (4)

<400> SEQUENCE: 2
tgacaattaa tcatcggctc gtatattgtg tggaattgtg agcggataac aatttcacac      60
aggaaacaga ttcccgggg aaaggattac aaa                                   93

<210> SEQ ID NO 3
<211> LENGTH: 112
<212> TYPE: DNA
<213> ORGANISM: Artificial Sequence
<220> FEATURE:
<223> OTHER INFORMATION: Tac2 promoter (4)

<400> SEQUENCE: 3
tgacaattaa tcatccggct cgtataatgt taacaatttg tggaattgtg agcggacaca      60
caggaaacag accatggaat tcgagctcgg tacccgggga aaggattaca aa             112

<210> SEQ ID NO 4
<211> LENGTH: 30
<212> TYPE: DNA
<213> ORGANISM: Artificial Sequence
<220> FEATURE:
<223> OTHER INFORMATION: Trc promoter (1)

<400> SEQUENCE: 4
tgacaattaa tcatcggcct cgtataatgt                                       30

<210> SEQ ID NO 5
<211> LENGTH: 7
<212> TYPE: DNA
<213> ORGANISM: Artificial Sequence
<220> FEATURE:
<223> OTHER INFORMATION: Ribosome binding region

<400> SEQUENCE: 5 gaaagga                                                                7

<210> SEQ ID NO 6
<211> LENGTH: 7
<212> TYPE: DNA
<213> ORGANISM: Artificial Sequence
<220> FEATURE:
<223> OTHER INFORMATION: Spacer sequence
```

```
<400> SEQUENCE: 6 ttacaaa                                                                7
```

```
<210> SEQ ID NO 7
<211> LENGTH: 289
<212> TYPE: PRT
<213> ORGANISM: Artificial Sequence
<220> FEATURE:
<223> OTHER INFORMATION: amino acid sequence of an enzyme protein
      originated from Clostridium scindens
```

```
<400> SEQUENCE: 7
```

| | | | | | | | | | | | | | | |
|---|---|---|---|---|---|---|---|---|---|---|---|---|---|---|
| Met | Lys | His | Gly | Ile | Tyr | Tyr | Ala | Tyr | Trp | Glu | Gln | Glu | Trp | Ala | Ala |
| 1 | | | | 5 | | | | | 10 | | | | | 15 | |
| Asp | Tyr | Lys | Arg | Tyr | Val | Glu | Lys | Ala | Ala | Lys | Leu | Gly | Phe | Asp | Ile |
| | | | 20 | | | | | 25 | | | | | 30 | | |
| Leu | Glu | Val | Gly | Ala | Ala | Pro | Leu | Pro | Asp | Tyr | Ser | Ala | Gln | Glu | Val |
| | | 35 | | | | | 40 | | | | | 45 | | | |
| Lys | Glu | Leu | Lys | Lys | Cys | Ala | Asp | Asp | Asn | Gly | Ile | Gln | Leu | Thr | Ala |
| | 50 | | | | | 55 | | | | | 60 | | | | |
| Gly | Tyr | Gly | Pro | Ala | Phe | Asn | His | Asn | Met | Gly | Ser | Ser | Asp | Pro | Lys |
| 65 | | | | | 70 | | | | | 75 | | | | | 80 |
| Ile | Arg | Glu | Glu | Ala | Leu | Gln | Trp | Tyr | Lys | Arg | Leu | Phe | Glu | Val | Met |
| | | | | 85 | | | | | 90 | | | | | 95 | |
| Ala | Gly | Leu | Asp | Ile | His | Leu | Ile | Gly | Ala | Leu | Tyr | Ser | Tyr | Trp |
| | | | | 100 | | | | | 105 | | | | | 110 | |
| Pro | Val | Asp | Phe | Ala | Thr | Ala | Asn | Lys | Glu | Glu | Asp | Trp | Lys | His | Ser |
| | | | 115 | | | | | 120 | | | | | 125 | | |
| Val | Glu | Gly | Met | Gln | Ile | Leu | Ala | Pro | Ile | Ala | Ser | Gln | Tyr | Gly | Ile |
| | | 130 | | | | | 135 | | | | | 140 | | | |
| Asn | Leu | Gly | Met | Glu | Val | Leu | Asn | Arg | Phe | Glu | Ser | His | Ile | Leu | Asn |
| 145 | | | | | 150 | | | | | 155 | | | | | 160 |
| Thr | Ser | Glu | Glu | Gly | Val | Lys | Phe | Val | Thr | Glu | Val | Gly | Met | Asp | Asn |
| | | | | 165 | | | | | 170 | | | | | 175 | |
| Val | Lys | Val | Met | Leu | Asp | Thr | Phe | His | Met | Asn | Ile | Glu | Glu | Ser | Ser |
| | | | 180 | | | | | 185 | | | | | 190 | | |
| Ile | Gly | Asp | Ala | Ile | Arg | His | Ala | Gly | Lys | Leu | Leu | Gly | His | Phe | His |
| | | 195 | | | | | 200 | | | | | 205 | | | |
| Thr | Gly | Glu | Cys | Asn | Arg | Met | Val | Pro | Gly | Lys | Gly | Arg | Thr | Pro | Trp |
| | 210 | | | | | 215 | | | | | 220 | | | | |
| Arg | Glu | Ile | Gly | Asp | Ala | Leu | Arg | Glu | Ile | Glu | Tyr | Asp | Gly | Thr | Val |
| 225 | | | | | 230 | | | | | 235 | | | | | 240 |
| Val | Met | Glu | Pro | Phe | Val | Arg | Met | Gly | Gly | Gln | Val | Gly | Ser | Asp | Ile |
| | | | | 245 | | | | | 250 | | | | | 255 | |
| Lys | Val | Trp | Arg | Asp | Ile | Ser | Lys | Gly | Ala | Gly | Glu | Asp | Arg | Leu | Asp |
| | | | 260 | | | | | 265 | | | | | 270 | | |
| Glu | Asp | Ala | Arg | Arg | Ala | Val | Glu | Phe | Gln | Arg | Tyr | Met | Leu | Glu | Trp |
| | | | 275 | | | | | 280 | | | | | 285 | | |
| Lys | | | | | | | | | | | | | | | |

```
<210> SEQ ID NO 8
<211> LENGTH: 870
<212> TYPE: DNA
<213> ORGANISM: Artificial Sequence
<220> FEATURE:
<223> OTHER INFORMATION: modified nucleic acid sequence (1) of the
      enzyme protein of SEQ ID NO: 7
```

<400> SEQUENCE: 8

```
atgaaacacg gtatctacta cgcgtactgg gaacaggaat gggcggcgga ctacaaacgt    60
tacgttgaaa aagcggcgaa actgggtttc gacatcctgg aagttggtgc ggcgccgctg   120
ccggactact ctgcgcagga agttaaagaa ctgaaaaaat gcgcggacga caacggtatc   180
cagctgaccg cgggttacgg tccggcgttc aaccacaaca tgggttcttc tgacccgaaa   240
atccgtgaag aagcgctgca gtggtacaaa cgtctgttcg aagttatggc gggtctggac   300
atccacctga tcggtggtgc gctgtactct tactggccgg ttgacttcgc gaccgcgaac   360
aaagaagaag actggaaaca ctctgttgaa ggtatgcaga tcctggcgcc gatcgcgtct   420
cagtacggta tcaacctggg tatggaagtt ctgaaccgtt cgaatctca catcctgaac    480
acctctgaag aaggtgttaa attcgttacc gaagttggta tggacaacgt taaagttatg   540
ctggacacct ccacatgaa catcgaagaa tcttctatcg gtgacgcgat ccgtcacgcg    600
ggtaaactgc tgggtcactt ccacaccggt gaatgcaacc gtatggttcc gggtaaaggt   660
cgtacccccgt ggcgtgaaat cggtgacgcg ctgcgtgaaa tcgaatacga cggtaccgtt   720
gttatggaac cgttcgttcg tatgggtggt caggttggtt ctgacatcaa agtttggcgt   780
gacatctcta aaggtgcggg tgaagaccgt ctggacgaag acgcgcgtcg tgcggttgaa   840
ttccagcgtt acatgctgga atggaaataa                                    870
```

<210> SEQ ID NO 9
<211> LENGTH: 870
<212> TYPE: DNA
<213> ORGANISM: Artificial Sequence
<220> FEATURE:
<223> OTHER INFORMATION: modified nucleic acid sequence(2) of the enzyme protein of SEQ ID NO:7

<400> SEQUENCE: 9

```
atgaagcacg gcatctacta cgcatactgg gagcaggagt gggcagcaga ctacaagcgc    60
tacgttgaga aggcagcaaa gctgggcttc gacatcctgg aggttggcgc agcaccactg   120
ccagactact ccgcacagga ggttaaggag ctgaagaagt gcgcagacga caacggcatc   180
cagctgaccg caggctacgg cccagcattc aaccacaaca tgggctcctc cgacccaaag   240
atccgcgagg aggcactgca gtggtacaag cgcctgttcg aggttatggc aggcctggac   300
atccacctga tcggcggcgc actgtactcc tactggccag ttgacttcgc aaccgcaaac   360
aaggaggagg actggaagca ctccgttgag ggcatgcaga tcctggcacc aatcgcatcc   420
cagtacggca tcaacctggg catggaggtt ctgaaccgct cgagtcccca catcctgaac   480
acctccgagg agggcgttaa gttcgttacc gaggttggca tggacaacgt taaggttatg   540
ctggacacct ccacatgaa catcgaggag tcctccatcg gcgacgcaat ccgccacgca    600
ggcaagctgc tgggccactt ccacaccggc gagtgcaacc gcatggttcc aggcaagggc   660
cgcaccccat ggcgcgagat cggcgacgca ctgcgcgaga tcgagtacga cggcaccgtt   720
gttatggagc cattcgttcg catgggcggc caggttggct ccgacatcaa ggtttggcgc   780
gacatctcca agggcgcagg cgaggaccgc ctggacgagg acgcacgccg cgcagttgag   840
ttccagcgct acatgctgga gtggaagtaa                                    870
```

METHOD FOR PRODUCING PSICOSE FROM FRUCTOSE-CONTAINING SUBSTRATE

TECHNICAL FIELD

The present invention relates to a method of obtaining a psicose-containing product from a fructose-containing substrate with high productivity in a short time at an industrial scale by an immobilization reaction using a biocatalyst for producing a psicose, and a method of preparing a liquid type or powder type of psicose continuously by isolating the psicose-containing product obtained by the method.

BACKGROUND ART

The development of biological methods for preparing a saccharide syrup has been focused mainly on producing a specific saccharide at the high concentration with high conversion rate by using an enzyme or a microbial cell.

The reason for such a development of production of saccharide syrup is, since a following process such as concentration, etc. after production of saccharide syrup is needed, to minimize the need of such a following process and reduce cost and time taken for isolation and purification of specific saccharide by producing the specific saccharide with high purity.

Recently, since a saccharide syrup having a specific composition has excellent sweetness quality and sweetness degree, there is a need to minimize the performance of additional concentration, isolation and purification processes, to manufacture the produced syrup itself or after passing through the minimal following process.

In addition, there is a need to produce a syrup containing a specific saccharide with high productivity within a short time on an industrial scale, and also there is a need to prepare the syrup stably.

DISCLOSURE

Technical Problem

The present invention provides a method of preparing a psicose-containing product from a fructose-containing substrate with high productivity on an industrial scale by an immobilization reaction using a biocatalyst for producing a psicose.

In addition, the present invention provides a method of preparing a liquid type or powder type of psicose by isolating the psicose-containing product obtained by the method.

Technical Solution

An embodiment of the present invention relates to a method for preparing a psicose-containing product from a fructose-containing substrate by an immobilization reaction using a biocatalyst for producing a psicose.

More specifically, the present invention relates to a method for preparing a psicose-containing product including less than 20% by weight total solid content of psicose and glucose, based on 100% by weight solid content of psicose, glucose and fructose in the product, by carrying out an immobilization reaction at the reaction velocity of 8.5 to 20, based on 1 of the reaction flow rate at which the psicose contained in the psicose-containing product is produced at an amount of 25% by weight or higher with respect to 100% by weight solid content of the total saccharides in the psicose-containing product.

Another embodiment of the present invention relates to a method for preparing a psicose as a liquid or powder product by preparing a psicose-containing product from a fructose-containing substrate by an immobilization reaction using a biocatalyst for producing a psicose, isolating a psicose fraction including 80% by weight or more or 90% by weight or more (e.g. 90% by weight) of psicose content and a raffinate fraction with a saccharide composition including 5% or less of psicose content by using a high-purity separation device, and performing an additional process in case of psicose fraction.

Hereinafter, the present invention will be described in more detail.

One embodiment of the present invention relates to a method for preparing a psicose-containing product from a fructose-containing substrate by an immobilization reaction using a biocatalyst for producing a psicose.

The substrate used for the immobilization reaction is a fructose-containing substrate, and the content of fructose used as a substrate for effective production of psicose may be 75 to 95% (w/v), for example, 80 to 91% (w/v), based on 100 (w/v) % solid content of total fructose-containing substrate. The fructose may be used for a method for preparing a psicose-containing product as a liquid form dissolved in a buffer solution or water (for example, distilled water). The fructose-containing substrate is not particularly limited, as long as containing fructose used for a psicose conversion reaction, and for example, may be an isomerized saccharide syrup. When the isomerized saccharide syrup is used as a substrate for produce a psicose, an isomerized saccharide syrup production process and a psicose production process may be proceeded continuously as a series of processes.

The psicose-containing product obtained according to the present invention may contain not only psicose but also fructose, glucose and various oligosaccharides. The total content of psicose and glucose comprised in the product may be less than 20% by weight, when the total content of fructose, glucose and psicose comprised in the psicose-containing product is 100% by weight, and for example, may be 9% by weight or more to less than 20% by weight. When the total content of fructose, glucose and psicose comprised in the product is 100% by weight, the total solid content of psicose and glucose is 9% by weight or more to less than 20% by weight, and the fructose content is over 80% by weight to 91% by weight. The psicose content comprised in the product may be 4% by weight to 29% by weight, when the total content of fructose, glucose and psicose is 100% by weight.

The biocatalyst for producing a psicose applicable for the present invention, for example, an enzyme or a microbial cell may be affected by a factor such as conversion reaction temperature, reaction time, fructose content of substrate, etc. For example, it may be used, in which a conversion rate of psicose from a substrate within 1 hour at the reaction temperature of 50 to 60 is 4 to 29%.

The biocatalyst may be a psicose conversion enzyme or a microbial cell for producing a psicose conversion enzyme, and the enzyme or microbial cell may be comprised in a bead, thereby being filled to a column for an immobilization reaction.

In case that the biocatalyst for producing a psicose is a microbial cell, it may be a recombinant strain in which a gene encoding a strain for producing a psicose epimerase or a psicose epimerase is introduced.

In a specific embodiment of the present invention, a strain producing a psicose epimerase may be a strain which has a high stability and can produce a psicose epimerase with high yield, and the recombinant strain may use various host cells, for example, *E. coli, Bacillus* sp. strain, *Salmonella* sp. strain and *Corynebacterium* sp. strain, etc., but preferably it may be *Corynebacterium* sp. strain, which is a GRAS strain, and may be *Corynebacterium glutamicum*.

In case of using a recombinant strain, a psicose epimerase can use an encoding gene of enzymes derived from various strains, and for example, it may be an enzyme derived from *Treponema primitia* disclosed in Korean Patent Publication No. 2014-0021974, an enzyme derived from Ruminococcus torques disclosed in Korean Patent Publication No. 2014-0080282 and an enzyme derived from *Clostridium scindens* disclosed in Korean Patent No. 10-1318422, and may also be an enzyme derived from *Ensifer adhaerens*. In one specific embodiment, a psicose epimerase according to the present invention may be an enzyme derived from *Clostridium scindens*, and for example, may comprise an amino acid sequence of SEQ ID NO: 7, and may be encoded by a base sequence comprising a nucleic acid sequence of and preferably comprises the nucleic acid sequence of SEQ ID NO: 1 as a core region. The trc promoter is an *E. coli*-derived promoter and is prepared by the combination of trp promoter and lac UV5 promoter. The tac1 promoter is an *E. coli*-derived promoter and is prepared by the combination of trp promoter and lac UV5 promoter. The tac2 promoter is an *E. coli*-derived promoter and is prepared by the combination of trp promoter and lac UV5 promoter, and is an optimized form by modifying the sequence of Tac 1 promoter.

The ribosome binding region and spacer may be chemically linked directly or indirectly linked by interposing a linker nucleic acid sequence in between. In one embodiment of the present invention, the ribosome binding region and spacer sequence may comprise one oligonucleotide sequentially linked in the 5' to 3' order. The nucleic acid sequences of promoter sequence, ribosome binding region and spacer sequence according to the one embodiment of the present invention is shown in the following Table 1. The bold underlined portions in Table 1 indicate ribosome binding region, spacer sequence, linker sequence, etc. in the regulatory sequence.

TABLE 1

| SEQ ID NO | Sequence (5'→3') | Name |
|---|---|---|
| 1 | aagcgcctcatcagcggtaaccatcacgggttcgggtgcgaaaaaccatgccataacaggaa tgttccttcgaaaattgaggaagcctttatgcccttcaaccctacttagctgccaattattc cgggcttgtgacccgctacccgataaataggtcggctgaaaaatttcgttgcaatatcaaca aaaaggcctatcattgggaggtgtcgcaccaagtacttttgcgaagcgccatctgacggatt ttcaaaagatgtatatgctcggtgcggaaacctac gaaaggatttttacccatggctgtatacgaactcccagaactcgactacgcatacgac gaaaggattacaaa | Sod promoter |
| 2 | tgacaattaatcatcggctcgtatattgtgtggaattgtgagcggataacaatttcacaca ggaaacagaattcccggggaaaggattacaaa | tac1 promoter |
| 3 | tgacaattaatcatccggctcgtataatgttaacaatttgtggaattgtgagcggacacac aggaaacagaccatggaattcgagctcggtacccggggaaaggattacaaa | Tac2 promoter |
| 4 | tgacaattaatcatcggcctcgtataatgt | trc promoter |
| 5 | gaaagga | Ribosome binding region |
| 6 | ttacaaa | Spacer sequence |

SEQ ID NO: 8 or SEQ ID NO: 9. The nucleic acid sequence of SEQ ID NO: 8 is *E. coli* optimized nucleic acid sequence, and SEQ ID NO: 9 is a nucleic acid sequence modified appropriately for *Corynebacterium*.

In the preparation of a recombinant strain according to one embodiment of the present invention, expression of an enzyme can be regulated using a regulatory sequence positioned on the top of the nucleic acid sequence encoding psicose epimerase, and the regulatory sequence essentially comprises a transcriptional promoter, and it may further comprise a ribosome-binding region and/or a spacer sequence. The elements constituting the regulatory sequence may be directly linked or linked by including one or more linkers of a nucleic acid sequence having 1 to 100 bases, for example, 5 to 80 bases.

In one specific embodiment, the transcriptional promoter may be a nucleic acid molecule expressing a nucleic acid sequence encoding a psicose epimerase in a *Corynebacterium* sp. strain, but may be tac1, tac2, trc, sod promoter. The sod promoter is derived from *Corynebacterium glutamicum*, It is preferable that the psicose epimerase according to the present invention is excellent in enzyme activity and thermal stability, and in the specific embodiment of the present invention, the combination of a transcriptional promoter or a regulatory sequence with a gene encoding a psicose epimerase, and all of tact, tac2, trc, trip, sod promoters can provide more than adequate protein expression with the psicose epimerase used in the present invention, and when sod promoter is used, it is more preferable, as the result that protein folding is robust and thermal stability is high can be obtained.

A method for producing psicose using a recombinant strain, etc. may be conducted by methods disclosed in Korean Patent Publication No. 2014-0021974, Korean Patent Publication No. 2014-0080282 and Korean Patent No. 10-1318422, but not particularly limited thereto.

The method for producing a psicose comprises a step of reacting the *Corynebacterium* sp. Strain with a fructose-containing raw material. In one specific embodiment, the step of reacting the *Corynebacterium* sp. Strain with a fructose may be conducted by a step of contacting a fructose into a carrier in which the strain or enzyme is immobilized. A psicose may be produced from a fructose reacting the immobilization enzyme or microbial cell with a fructose-containing substrate, thereby converting a fructose into a psicose.

In the method for producing a psicose, the reaction may be performed under the condition of pH 6 to 9.5, for example, pH 7 to 9, pH 7 to 8, or pH 8 to 9.

In addition, the reaction may be performed under the temperature condition of 30° C. or higher, for example, 40° C. When the temperature is 80° C. or higher, the browning phenomenon of fructose which is a substrate may be occurred, and therefore the reaction may be performed under the condition of 40 to 80° C., for example, 50 to 75° C., 60 to 75° C., or 68 to 75° C.

When the reaction time is longer, the psicose conversion rate is increased, and when the reaction time is shorter, the productivity becomes enhanced. For example, it is preferable that the reaction time is 0.5 hours (30 min) or longer, 1 hour or longer, 2 hours or longer, 3 hours or longer, 4 hours or longer, 5 hours or longer or 6 hours or longer. Since the rate of increase of psicose conversion rate is insignificant or rather decreased, when the reaction time is over 48 hours, it is preferable that the reaction time is 48 hours or less. Thus, the reaction time may be 0.5 to 48 hours, 1 to 48 hours, 2 to 48 hours, 3 to 48 hours, 4 to 48 hours, 5 to 48 hours, or 6 to 48 hours, and regarding industrial and economical aspects, may be approximately 0.5 to 48 hours, 0.5 to 36 hours, 0.5 to 24 hours, 0.5 to 12 hours, or 0.5 to 6 hours, but not limited thereto. The condition is selected as a condition in which the efficiency from a fructose into a psicose is maximized.

The activation of the enzyme converting a fructose into a psicose (for example, epimerase) may be controlled by a metal ion, and therefore, for the production of psicose, when the metal ion is added, the efficiency of conversion from a fructose into a psicose, namely the production of psicose may be increased.

Thus, the composition for producing a psicose including the *Corynebacterium* sp. Strain may further comprise a metal ion. In addition, the method for producing a psicose using the *Corynebacterium* sp. Strain may further comprise a step of adding a metal ion. In one specific embodiment, the metal ion may be added into a culture medium of the culturing step, or the culturing step may be performed in the culture medium in which the metal ion is added. In other embodiment, the metal ion may be added into a fructose, or may be added into a carrier in which the *Corynebacterium* sp. strain is immobilized (before adding a fructose), or may be added into a mixture of a carrier in which the *Corynebacterium* sp. strain is immobilized and a fructose (after adding a fructose), or may be added at the time of adding a fructose in a form of mixture or respectively.

The metal ion may be one or more kinds selected from the group consisting of copper ion, manganese ion, calcium ion, magnesium ion, zinc ion, nickel ion, cobalt ion, iron ion, aluminum ion, etc. For example, the metal ion may be one or more kinds selected from the group consisting of manganese ion, magnesium ion, nickel ion and cobalt ion, etc., and in one embodiment, the metal ion may be a manganese ion, cobalt ion, or the mixture thereof. When the amount of metal ion added is less than 0.5 mM, the effect of psicose production yield enhancement is insignificant, and therefore, the amount of metal ion added may be 0.5 mM or more. On the other hand, since the effect is insignificant compared to its excess, when the amount of metal ion added is over 5 mM, the amount of metal ion added is 5 mM or less. For example, the amount of metal ion added may be in the range of 0.5 mM to 5 mM, for example, 0.5 mM to 2 mM.

When an enzyme or a microbial cell for producing a psicose according to the present invention is used as immobilized into a carrier, the carrier may create environment to maintain the activity of immobilized strain or the enzyme produced from the strain for a long time, and may be all of publicly known carriers available for a use of enzyme immobilization. For example, sodium alginate as the carrier may be used. The sodium alginate is natural colloidal polysaccharide plentifully present in a cell wall of seaweed, and is composed of mannuronic acid (β-D-mannuronic acid) and gluronic acid (α-L-gluronic acid), and in the content aspect, is randomly formed by making a β-1,4 bond, thereby stably immobilizing a strain or enzyme, and thus it may be advantageous to show an excellent psicose yield.

In one specific embodiment, to more enhance the yield of psicose, the sodium alginate solution of 1.5 to 4.0% (w/v) concentration (for example, sodium alginate aqueous solution), for example, the sodium alginate of 2.0% (w/v) may be used for immobilization of strain. For example, a microbial cell of strain, culture including an enzyme produced by the strain, or lysate of the strain may be immobilized into the sodium alginate carrier, by dropping the obtained mixture solution into approximately 0.2M calcium ion solution using an injection pump and vacuum pump, thereby producing a bead, after adding a microbial cell of strain, culture including an enzyme producing the strain, or lysate of the strain into 1 to 2 volume times of sodium alginate aqueous solution of a microbial cell of strain, culture including an enzyme producing the strain, or lysate of the strain. The enzyme may be purified by a method such as a common method, for example, dialysis, precipitation, adsorption, electrophoresis, affinity chromatography, ion exchange chromatography, etc., form the strain, strain culture or lysate of the strain.

The carrier in which the microbial cell or enzyme is supported, for example, bead may a bead for producing a psicose which reduces the bead size and reduce swelling by compression processing a bead, thereby increasing the production of psicose and is capable of being used stably for a long period.

One embodiment may be a compressed bead compression processed which comprises an enzyme or microbial cell for producing a psicose and an alginate acid or its salt as a carrier, and may be a bead for producing a psicose which has 62 to 100 average diameter of compressed bead based on 100 average diameter of bead before a compression process. The compressed bead may reduce a swelling phenomenon when reacted with a liquid substrate, and specifically, the swelling rate of average diameter of bead may be 100 to 155, for example, 100 to 130, or 100 to 125, etc., based on 100 swelling rate of bead diameter before contacting with the liquid substrate.

The method for preparing a compressed bead according to the present invention may comprise a method of treating a metal ion and a method of treating a metal ion and coating with a swelling inhibitor, and freeze-drying method. The metal ion of bead compression processing may be one or more kinds of divalent metal ions selected from the group consisting of $Mn^{2+}$, $Zn^{2+}$, $Co^{2+}$, $Mg^{2+}$, $Ni^{2+}$, $Fe^{2+}$, and $Cu^{2+}$, and the swelling inhibitor may be one or more kinds selected from the group consisting of chitosan, chitin, polyethylene glycol (PEG), polyethylene imine (PEI), chito-oligosaccharide and polylysine. The freeze-drying method may be performed by freezing in the temperature range of −90° C.

to −10° C., and drying the temperature range of −40° C. to 20° C. under the pressure of less than 10 mtorr.

In case of bead in which the compression processing is performed by a method of treating a metal ion and a method of treating a metal ion and coating with a swelling inhibitor, a desirable percentage of moisture content may be 50 to 88%. In addition, in case of compressed bead prepared by a freeze-drying, a desirable percentage of moisture content may be 10 to 50%.

The present invention relates to a method for preparing a liquid or powder psicose by performing a separation process from a psicose-containing product from a fructose-containing substrate by an immobilization reaction using a biocatalyst for producing a psicose.

One specific embodiment relates to a method for preparing a psicose obtaining a psicose-containing liquid product comprising, preparing a psicose-containing product from a fructose-containing substrate by an immobilization reaction using a biocatalyst for producing a psicose according to the present invention;

decoloring or desalting the produced psicose-containing product, and concentrating the decolored or desalted product to 75 Brix (%) or more solid content of psicose.

Another embodiment relates to a method of preparing a psicose-containing powder, comprising 1preparing a psicose-containing product from a fructose-containing substrate by an immobilization reaction using a biocatalyst for producing a psicose;

decoloring or desalting the produced psicose-containing product, separating the decolored or desalted product to separate a psicose fraction of 90% by weight or more psicose content and a raffinate fraction having a saccharide composition of 5% or less of psicose content;

concentrating the separated psicose fraction;

crystallizing the concentrate in a psicose supersaturated state; and separating the crystallized psicose from a crystal mother liquor and drying.

The psicose-containing product collected from a fructose by the method of the present invention may be achieved by a common method, one or more methods such as desalting, decoloring, concentration, high purity separation purification using SMB chromatography, crystallization, centrifugation, filtration, etc. The crystallization step may crystallizing a psicose by making the psicose in the supersaturated state, and one example of method for reaching the supersaturated state may be a method of cooling a psicose-containing solution, but not limited thereto.

The basic principle of SMB used in the purification step using the SMB chromatography is to copy the flow of countercurrent of immobilized phase and mobile phase and to make continuous separation available by moving the position between columns at the certain time interval. Materials moving fast due to weak affinity with an absorbent are collected to a fraction including a high purity psicose separated by moving to the direction of liquid flow, and materials moving slowly due to strong affinity with an absorbent are collected to a raffinate fraction having a saccharide composition of 5% or less psicose content separated by moving to the direction of immobilized phase flow. Columns are continuously linked, and the entrance is composed of mixture and mobile phase, and the exit is composed of high purity psicose fraction and a fraction including a low content of psicose. SMB is commonly consisted of 4 areas, and is divided according to the position of entrance and exit. SMB technology may make continuous separation possible and obtain high concentration and high yield of product, compared to batch separation process. SMB experiment may be performed by determining a specific condition with respect to basic factors such as adsorption ratio, diffusion and dispersion of each material.

Psicoses may be prepared continuously, by separating the fractionized high purity psicose and separated raffinate fraction having a saccharide composition of 5% or less psicose content.

Effect of the Invention

The present invention is a method of preparation of psicose-containing product from a fructose-containing substrate by an immobilization reaction using a biocatalyst for producing a psicose and a method for continuously preparing a liquid or powder psicose by isolating the psicose-containing product obtained by the method, and has an advantage of obtaining a psicose with high productivity within a short time on an industrial scale.

BRIEF DESCRIPTION OF DRAWINGS

FIG. 1 is a graph showing the change of psicose content in the product depending on the column flow rate in the range of liquid fructose content of 75% to 95% and the range of 5% to less than 20% of the total content of glucose and psicose, in the psicose production by using an immobilization reaction filled with bead containing a cell for producing a psicose, according to an Example of the present invention.

FIG. 2 is a formula showing the change of psicose content in the product depending on to column flow rate in the range of liquid fructose content of 75% to 95% and the range of 5% to less than 20% of total content of glucose and psicose, in the psicose production by using an immobilization reaction filled with bead containing a cell for producing a psicose according to an Example of the present invention.

FIG. 3 shows an example of recombinant expression vector for preparing a psicose syrup of the present invention (pCES_sodCDPE).

FIG. 4 is a process diagram showing a psicose production procedure according to an example of the present invention.

DETAILED DESCRIPTION OF THE EMBODIMENTS

Example 1: Establishment of Psicose Production System 1-1: Preparation of a Strain Producing Psicose The gene encoding a psicose epimerase derived from *Clostridiuim scindens* (*Clostridiuim scindens* ATCC 35704) (DPE gene; Gene bank: EDS06411.1) was synthesized as a modified polynucleotide form optimized for *E. coli* and called CDPE. The polynucleotide optimized for *E. coli* and sod promoter and T7 terminator obtained from pET21a vector were obtained as each template through PCR, and these were linked as one template by overlap PCR method and cloned into pGEM T-easy vector through T-vector cloning, to confirm the sequence including sod promoter (SEQ ID NO: 1), optimized CDPE sequence of SEQ ID NO: 8 and T7-terminator.

The whole polynucleotide was inserted into the same restriction enzyme site of an expression vector pCES208 (J.

Microbiol. Biotechnol., 18:639-647, 2008) with restriction enzymes NotI and XbaI(NEB), to produce a recombinant vector pCES208/psicose epimerase (pCES_sodCDPE). The cleavage map of the produced recombinant vector (pCES_sodCDPE) was shown in FIG. 1.

*Corynebacterium glutamicum* was transformed with the prepared recombinant vector (pCES_sodCDPE) using electroporation. Colonies were picked and inoculated in 4 ml of LB medium (tryptone 10 g/L, NaCl 10 g/L, yeast extract 5 g/L) supplemented with Kanamycin at final concentration of 15 ug/ml, and then cultured for approximately 16 hours under the culture conditions of 30° C. and 250 rpm. Then, 1 ml of the culture solution was collected and inoculated in 100 ml LB medium including 15 ug/ml of Kanamycin, and the culture was continued for over 16 hours. After lysis of cultured cells with beadbeater, only supernatant was obtained and mixed with a sample buffer at a mixing ratio of 1:1, and then heated at 100° C. for 5 minutes. The prepared samples were subjected to electrophoresis on a 12% SDS-PAGE gel (composition: running gel—3.3 ml H2O, 4.0 ml 30% acrylamide, 2.5 ml 1.5M Tris buffer (pH 8.8), 100 μl 10% SDS, 100 μl, 10% APS, 4 μl TEMED/stacking gel—1.4 ml H2O, 0.33 ml 30% acrylamide, 0.25 ml 1.0M Tris buffer (pH 6.8), 20 μl 10% SDS, 20 μl 10% APS, 2 μl TEMED) at 180V for approximately 50 minutes, to confirm the protein expression. After the expression of CDPE was confirmed on the SDS-PAGE gel, His-tag purification was proceeded using Ni-NTA resin and the expression rate was calculated using a calculation formula (expression rate (%)=(Purified protein (mg)/Total soluble protein (mg))×100), for accurate measurement of expression level. The prepared *Corynebacterium glutamicum* transformant produced 16.62 mg of the total water-soluble proteins and 1.74 mg of purified enzyme protein.

1-2: Preparation of Immobilization Bead

In order to prepare psicose from fructose using the recombinant strain producing psicose epimerase in Example 1-1, the cells were collected by centrifugation in the cell culture.

Then, the cell suspension was treated with 0.05% (v/v) of en emulsifier (Ryoto(tkSugar Ester, M-1695) in a final volume and treated at 35° C. (±5° C.) for 60 minutes. When the reaction was completed, the microbial cells were collected after removing the supernatant containing the emulsifier again by centrifugation.

To prepare immobilized beads, the collected microbial cells were mixed with distilled water to a final microbial cell concentration of 5% (v/v), and 5% (v/v) of the collected microbial cells were mixed with 4% (v/v) of alginic acid dissolved in water at a mixing ratio of 1:1, and refrigerated at 4° C. to remove bubbles generated during mixing. The refrigerated mixture solution was extruded through Needle (inner diameter 0.20~0.30 mm) and formed into a droplet shape due to the weight, and the dropped mixture solution was cured by being dropped into the prepared 100 mM calcium chloride (CaCl$_2$) solution, to form spherical or elliptical beads (diameter 2.0~2.2 mm). The formed beads were soaked in a 100 mM calcium chloride solution and mixed evenly by a stirrer so as to be further cured.

After all mixture solution was extruded, the beads were further cured by keeping refrigerator for 4~6 hours, and then cured for approximately 6 hours in a refrigerated state with replacing with a new 100 mM calcium chloride solution. After the beads were completely cured, the beads were skimmed and the moisture was removed completely. The beads were stirred for 10 minutes after addition of water at 3 times as much as the volume of the beads. The process was repeated three times to remove the calcium chloride solution. After completely removing moisture of washed beads, a fructose-containing substrate (50 brix of fructose and 1 mM MnCl$_2$·4H$_2$O) was inputted at 3 times as much as the volume of the beads, and then it was stirred for 10 minutes. Such treatment was carried out at 2 times or more to replace with a fructose-containing substrate used as a reaction substrate. The reaction substrate was adjusted to pH 6.8~7.2 with 3N NaOH. The liquid fructose or crystalline fructose can be used as the substrate depending on the product kinds.

The beads replaced with the reaction substrate were filled into an immobilization reaction column, and then used for producing a psicose syrup.

1-3: Preparation of Psicose Syrup

After filling the prepared beads in Example 1-2 into an immobilization reaction column, a psicose syrup was produced under the following reaction conditions. A raw material which was 50% of solid content, and included 88.8% by weight of fructose and 4.8% by weight of glucose, among 100% by weight of solid content of total saccharides of fructose-containing substrate (pH 6.8~7.1) with 50% (w/w) or more of solid content, was provided to the following immobilization reaction column, thereby preparing the mixed saccharide of the psicose syrup.

Immobilization Column Reaction Conditions (1) Reaction temperature: 50 r of internal temperature of the column jacket
(2) Reaction substrate: substrate containing 88.8% by weight of fructose and 4.8% by weight of glucose in the total solid content of fructose-containing substrate with 50% (w/w) or higher of solid content, and including less than 6.4% by weight of other saccharides of 1 or higher DP (Degree of Polymerization) except for the fructose and glucose.
(3) Production standard: production of syrup including 24% by weight of psicose content in 100% by weight of solid content of total saccharides in the product.

As the result of the reaction, 24% by weight of psicose syrup with the weight ratio of glucose:fructose:psicose:oligosaccharide of 5:65:24:6 was collected from the reaction solution.

Example 2: Psicose Production Depending on the Increased Reaction Flow Rate

After filling beads prepared in Example 1-2 into an immobilization reaction column, the amounts of produced psicose syrup depending on the column flow rate under the following reaction conditions were compared by feeding the reaction substrates at 5 times of column volume for 1 hour according to the ratio of increased flow rate, at the point when the psicose content (%) in the column was stabilized. The column was fed by a raw material of reaction substrate solution with 50% (w/w) of solid content including 88.8% by weight or more of the fructose content and 4.8% by weight of glucose content, based on 100% by weight of the solid content of total saccharides.

The analysis of saccharide content was detected with RI by injecting 10 μL of samples suitably diluted with water solvent at the flow rate of 0.6 ml/min by using Aminex HPX-87C column (80° C.) of Biorad company, and within 30 minutes of analysis time, the fructose, psicose and other DP 1 or more saccharides were integrated, thereby analyzing each area. In addition, to analyze the content by each saccharide composition, values corresponding to area by each saccharide composition were analyzed as the content of each saccharide, when the value of sum of total areas of fructose, psicose and other DP1 or more saccharides shown within 30 minutes of analysis time.

Immobilization Column Reaction Conditions (1) Reaction temperature: 50° C. of internal temperature of the column jacket,
(2) Reaction substrate: substrate including 88.8% by weight of fructose and 4.8% by weight of glucose among 100% by weight of solid of total saccharides of fructose-containing substrate with the solid content of 50% (w/w) (pH 6.8~7.2) and containing less than 6.4% of other saccharides of DP 1 or more except for fructose and glucose, which is a raw material including 94.9% by weight of fructose content and 5.1% by weight of glucose in the raw material substrate, when they were converted on the basis of 100% by weight of total content of fructose, glucose and psicose,
(3) Column flow rate: the psicose content in the product is evaluated depending on the ratio of increased flow rate, as the reaction is carried out by increasing the reaction flow rate by 1 to 20 times, based on 1 of the reaction flow rate at which the psicose contained in the psicose-containing product is produced at an amount of 25% by weight or higher with respect to 100% by weight solid content of the total saccharides in the psicose-containing product,
(4) Production standard: total content of glucose and psicose ranges from 9% by weight or more to less than 20% by weight, in 100% by weight of total content of fructose, glucose and psicose in the product.

The experimental result was shown in the following Table 2 and FIG. 1. In Table 2, contents of each saccharide were shown, based on 100% by weight of the total content of fructose, glucose and psicose in the solid content of total saccharides in the product.

TABLE 2

| Increase ratio of flow rate | Fructose content (wt %) | Psicose content (wt %) | Glucose content (wt %) | Total content of psicose and glucose (wt %) |
|---|---|---|---|---|
| Substrate before reaction | 94.9 | 0 | 5.1 | 5.1 |
| 1 | 67.8 | 27.1 | 5.1 | 32.2 |
| 2 | 69.7 | 25.2 | 5.1 | 30.3 |
| 4 | 73.5 | 21.4 | 5.1 | 26.5 |
| 6 | 76.7 | 18.2 | 5.1 | 23.3 |
| 8 | 79.6 | 15.3 | 5.1 | 20.4 |
| 10 | 81.8 | 13.1 | 5.1 | 18.2 |
| 12 | 83.8 | 11.1 | 5.1 | 16.2 |
| 16 | 87.5 | 7.4 | 5.1 | 12.5 |
| 20 | 90.3 | 4.6 | 5.1 | 9.7 |

As shown in Table 2, when the total solid content of fructose, glucose and psicose included in the reaction substrate was 100% by weight, a raw material including 94.9% of fructose content and 5.1% of glucose was used. Since the fructose was converted into psicose, as the conversion reaction was progressed, 94.9% of fructose content as the substrate was gradually reduced, and the psicose content was increased, with maintaining the same content of 5.1% of glucose.

According to the increase of column flow rate, the psicose conversion rate was gradually reduced. The psicose content was 4.6%, when reacted at the flow rate of 20 times higher than the flow rate of producing 27.1% psicose content in Table 2. When reacted at the flow rate increased 10 times higher than the flow rate of producing 25% psicose content of Example 1, a syrup composition having less than 20% by weight of total content of glucose and psicose was produced.

The change in psicose content by the change in the column flow rate in Table 2 was shown in FIG. 1, thereby showing the change in psicose content in the product according to the ratio of column flow rate increase.

As shown in FIG. 2, when numerical values of column flow rate were input into the formula, it could be seen that the production condition for syrup composition including 9.7% by weight or more to less than 20% by weight of total solid content of glucose and psicose, on the basis of 100% by weight of the total content of fructose, glucose and psicose in the product, could be controlled in 8.5 to 20 times of the flow rate for producing the syrup composition including 25% by weight of psicose content in Example 1. This result showed increased approximately 10 times higher than the flow rate for producing the syrup composition including 25% by weight of psicose content in Example 1, the column flow rate available for production of syrup composition having less than 20% by weight of total solid content of glucose and psicose, as the flow rate increased approximately 8.5 times higher than the flow rate for producing the syrup composition including 25% by weight of psicose content in Example 1.

In addition, as the result of analyzing the content of produced materials in which the production was completed in the reaction with 10 times higher of the column flow rate under the immobilization reaction conditions by using the formula of FIG. 2, a composition containing 76.5% by weight of fructose, 12.3% by weight of psicose, 4.8% by weight of glucose, and 6.4% of other saccharides of DP1 or more, based on 100% by weight of total saccharide solid content were obtained, when it was converted as 100% by weight of total content of fructose, glucose and psicose, the sum of psicose and glucose contents could be produced as 18.2% by weight.

Example 3: Evaluation of Reaction Stability

After filling beads prepared in Example 1-2 into an immobilization reaction column, the fructose-containing substrate and the reaction condition were the same as those of Example 2.

By using the formula of FIG. 2, the flow rate among column flow rate in which the total content of psicose and glucose was less than 20% by weight was selected and fixed, based on 100% by weight of the total content of fructose, glucose and psicose in the saccharides of the product, and the change in psicose content of the product was measured at different day numbers for reaction. Specifically, the result of measuring the change in psicose content contained in the product were shown in the following Table 3, by fixing the flow rate as 8.5 times higher than the flow rate of producing 25% by weight of psicose content in 100% by weight of solid content of total saccharides in Example 1 and reacting for 15 days.

Immobilization Reaction Conditions (1) Reaction temperature: 50° C.,
(2) Reaction substrate: the same reaction substrate of Example 2,
(3) Column condition: flow rate increased at 8.5 times higher than the flow rate of producing 25% by weight of psicose content in 10% by weight of solid content of total saccharides in Example 1, and
(4) Production standard: total content of glucose and psicose ranges from 15% by weight or more to less than 20% by weight, when the total content of fructose, glucose and psicose in the product was 100% by weight.

TABLE 3

| Reaction time (day) | Fructose content(wt %) | Psicose content (wt %) | Total content of psicose and glucose (wt %) |
|---|---|---|---|
| 0 | 80.5 | 14.4 | 19.5 |
| 1 | 80.1 | 14.8 | 19.9 |
| 2 | 80.1 | 14.8 | 19.9 |
| 4 | 80.1 | 14.8 | 19.9 |
| 6 | 80.1 | 14.8 | 19.9 |
| 8 | 80.1 | 14.8 | 19.9 |
| 9 | 80.2 | 14.7 | 19.8 |
| 12 | 80.3 | 14.6 | 19.7 |
| 13 | 80.5 | 14.4 | 19.5 |
| 14 | 80.6 | 14.3 | 19.4 |
| 15 | 80.7 | 14.2 | 19.3 |

As shown in Table 3, the psicose content in the product were measured during the reaction for 15 days at the high reaction flow rate, a composition including 10% by weight or more to less than 15% by weight of psicose content and 15% by weight or more to less than 20% by weight of total content of psicose and glucose, on the basis of 100% by weight of the total content of fructose, glucose and psicose, could be stably produced for 15 days.

Example 5: Continuous Recycle Production of Psicose

A psicose production system was established as a continuous production process by continuously producing a psicose syrup having less than 20% by weight of total content of glucose and psicose, when the total content of fructose, glucose and psicose contained in the product was 100% by weight, and separating a psicose fraction from the product and a fructose raffinate fraction.

Specifically, the psicose conversion reaction was performed by controlling the flow rate of psicose conversion reaction column under the condition of producing less than 20% by weight of glucose and psicose based on 100% by weight of total content of fructose, glucose and psicose contained in the product, and psicose fraction with 90% or more of psicose purity and fructose raffinate fraction containing excess amount of fructose were separated from the psicose-containing product by using high-purity separation process.

The schematic diagram of the entire reaction process of psicose production was shown in FIG. 4, and the process may be inserted or excluded according to a production quality or production process. The detailed production process was as follows.

After liquid fructose with 75 Brix (%) of solid content (when the total solid content was 100% by weight, the content of fructose was contained as 88.8% by weight) was added by water to 50 Brix (%) of the solid content, and adjusted to pH 7.0 by adding with 5N NaOH, to prepare a raw material of reaction. The raw material was provided into a reaction column which were filled with microbial cell immobilization beads of Example 1-2 (50° C. constant temperature) and a syrup containing less than 20% by weight of glucose and psicose was produced according to the substantially same method of Example 3, when the fructose in the raw material was converted into a psicose, on the basis of 100% by weight of the total content of fructose, glucose and psicose of reaction raw material.

As a process for separating the produced psicose syrup, the produced psicose-containing syrup was decolored at 50° C. for 30 minutes by adding 0.05% (w/w) of activated carbon to the solid content in the syrup, and the completely decolored psicose-containing syrup was passed through a micro filter, thereby removing the activated carbon.

The psicose-containing syrup in which the activated carbon was removed was desalted by flowing through the column filled with cation exchange resin, anion exchange resin and a mixed resin thereof at room temperature in order to remove impurities such as ion component, etc., at the volumetric rate of 2 times (1~2 times) of ion exchange resin per hour. The psicose was separated at the ratio of 0.15 based 1 of total solid weight in the raw material used for psicose conversion reaction, in the SMB (simulated moving bed) filled with calcium ($Ca^{2+}$) type ion exchange resin at the flow rate of 0.06SV, under the condition that the separation ratio of psicose:fructose was 0.7:1, to obtain a high-purity psicose fraction of 96% psicose purity with 4 Brix (%) of solid content. The triple-distilled water was used for the mobile phase of column because of food usage.

At the same time, raffinate fraction including 5.5% glucose, 83.9% fructose, 3.4% psicose, and 4.2% other saccharides as the content of composition except for the high-purity psicose fraction were collected at the ratio of 0.85, when the total solid weight of raw material used for psicose conversion reaction was 1. After the fractionized raffinate was transferred and set to the solid content 50 Brix (%) as the fructose-containing substrate of psicose conversion, and adjusted to pH 7.0 by using 5N NaOH, to be provided into a reaction column and recycled to perform a psicose conversion reaction.

The high-purity psicose separated in the SMB was transferred to a storage tank and concentrated to be the solid content 80 Brix (%) or more at 60° C., and was cooled to the supersaturated state according to the cooling crystallization method, to produce a psicose crystal. Then, the psicose powder with 99% psicose purity was finally obtained at 81% yield by centrifugal dehydration and drying.

The invention claimed is:

1. A method for preparing a psicose-containing product from a fructose-containing substrate by a reaction of fructose substrate using an immobilized biocatalyst for producing a psicose,
    wherein the immobilized biocatalyst is a psicose epimerase enzyme, or a microbial cell producing a psicose epimerase which is immobilized in a bead,
    wherein the biocatalyst has 20 to 29% of the conversion rate of psicose from the fructose-containing substrate comprising 75 to 95% by weight of fructose at a reaction temperature of 50 to 60° C. within one (1) hour,
    wherein the reaction is performed at the reaction flow rate of 8.5 to 20, based on 1 of the reaction flow rate at which the psicose contained in the psicose-containing product is produced at an amount of 25% by weight or higher with respect to 100% by weight solid content of the total saccharides in the psicose-containing product, and
    wherein the solid content of psicose and glucose is lower than 20% by weight, with respect to 100% by weight of solid content of psicose, glucose and fructose contained in the psicose-containing product.

2. The method of claim 1, wherein the solid content of psicose and glucose is 9% by weight or higher to lower than 20% by weight, based on 100% by weight total solid content of saccharide and psicose-containing product.

3. The method of claim 1, wherein the reaction is performed at the reaction flow rate of 10 to 18, based on 1 of the reaction flow rate at which the psicose contained in the psicose-containing product is produced at an amount of 25% by weight or higher with respect to 100% by weight solid content of the total saccharides in the psicose-containing product.

4. The method of claim 1, wherein the solid content of psicose and glucose is 9% by weight to lower than 20% by weight, and the solid content of fructose is 80 to 91% by weight, based on 100% by weight of total content of fructose, glucose and psicose in the psicose-containing product.

5. The method of claim 1, wherein the reaction is performed by using a substrate comprising 80% by weight to 95% by weight of fructose in 100% by weight of solid content of total saccharides in the fructose-containing substrate.

6. The method of claim 1, wherein the fructose-containing substrate is an isomerized saccharide syrup.

7. The method of claim 1, wherein the reaction is performed by using an immobilization column filled with a bead containing an enzyme for producing a psicose or a microbial cell producing a psicose.

8. The method of claim 7, wherein the reaction is performed by using a bead containing the microbial cell or enzyme which is treated with divalent metal ion and coated with one or more swelling inhibitors selected from the group consisting of chitosan, chitin, polyethylene glycol (PEG), polyethylene amine (PEI), chito-oligosaccharide and polylysine.

9. The method of claim 7, wherein the reaction is performed by using a bead containing the microbial cell or enzyme which is treated by freeze-drying and compressed.

10. The method of claim 8, wherein the microbial cell producing a psicose is a *Corynebacterium* strain transformed with a gene of psicose epimerase.

11. The method of claim 10, wherein the *Corynebacterium* strain is one or more kinds of *Corynebacterium* sp. strains selected from the group consisting of *Corynebacterium glutamicum, Corynebacterium acetoglutamicum, Corynebacterium acetoacidophilum, Corynebacterium thermoaminogenes, Corynebacterium melassecola* and *Corynebacterium efficiens*.

12. The method of claim 1, wherein the microbial cell producing a psicose is a strain producing a psicose epimerase.

13. The method of claim 1, wherein the reaction is performed at 40 to 80° C. for 0.5 to 48 hours.

14. A method for preparing a psicose by obtaining a psicose-containing liquid product comprising,
    obtaining a psicose-containing product according to claim 1,
    decoloring or desalting the produced psicose-containing product, and
    concentrating the decolored or desalted product to 75 Brix (%) or higher of solid content of psicose.

15. A method of preparing a psicose comprising preparing a psicose-containing powder comprising,
    obtaining a psicose-containing product according to claim 1,
    decoloring or desalting the produced psicose-containing product,
    separating the decolored or desalted product to separate a psicose fraction of 90% by weight or higher of psicose content and a raffinate fraction,
    concentrating the separated psicose fraction,
    preparing a concentrate in a psicose supersaturated state to crystallize a psicose, and
    separating the crystallized psicose from a crystal mother liquor and drying.

* * * * *